United States Patent [19]

Takahashi et al.

[11] Patent Number: 6,080,363
[45] Date of Patent: Jun. 27, 2000

[54] LIQUID TREATING APPARATUS FOR BIOLOGICAL SAMPLE

[75] Inventors: Tomio Takahashi, Nagano; Mamoru Wakabayashi, Koushoku; Hiroe Tateya, Nagano; Norihisa Ishizaka, Koushoku, all of Japan

[73] Assignees: Kabushiki Kaisha Tiyoda Seisadusho, Nagano-Ken; Sakura Finetechnical Co. Ltd., Tokyo-To, both of Japan

[21] Appl. No.: 09/068,651

[22] PCT Filed: Sep. 18, 1997

[86] PCT No.: PCT/JP97/03301

§ 371 Date: Oct. 14, 1998

§ 102(e) Date: Oct. 14, 1998

[87] PCT Pub. No.: WO98/12535

PCT Pub. Date: Mar. 26, 1998

[30] Foreign Application Priority Data

| Sep. 18, 1996 | [JP] | Japan | 8-246601 |
| Sep. 18, 1996 | [JP] | Japan | 8-246603 |
| Sep. 20, 1996 | [JP] | Japan | 8-249543 |
| Feb. 25, 1997 | [JP] | Japan | 9-040959 |
| Mar. 11, 1997 | [JP] | Japan | 9-056435 |

[51] Int. Cl.[7] .................................................. G01N 35/02
[52] U.S. Cl. .............................. 422/65; 422/63; 422/104; 436/46; 436/47; 436/48; 118/625; 427/2.11
[58] Field of Search ........................ 422/63, 65, 68.1, 422/81, 99, 100, 102, 103, 104; 436/43, 44, 46, 47, 48, 49, 174, 175, 180; 118/425; 427/2.11, 4

[56] References Cited

U.S. PATENT DOCUMENTS

| 3,807,353 | 4/1974 | Kobernick | 118/5 |
| 3,976,028 | 8/1976 | Howells et al. | 118/6 |
| 4,738,824 | 4/1988 | Takeuchi | 422/63 |
| 4,919,887 | 4/1990 | Wakatake | 422/67 |
| 5,122,342 | 6/1992 | McCulloch et al. | 422/65 |
| 5,345,395 | 9/1994 | Griner | 364/497 |
| 5,439,649 | 8/1995 | Tseung et al. | 422/99 |
| 5,523,056 | 6/1996 | Miller | 422/64 |
| 5,573,727 | 11/1996 | Keefe | 422/63 |
| 5,737,499 | 4/1998 | Bernstein et al. | 395/82 |
| 5,895,628 | 4/1999 | Heid et al. | 422/65 |

FOREIGN PATENT DOCUMENTS

| 5-11046 | 2/1993 | Japan . |
| 5-66543 | 3/1993 | Japan . |
| 6-100522 | 12/1994 | Japan . |
| 8-500434 | 1/1996 | Japan . |

*Primary Examiner*—Long V. Le
*Attorney, Agent, or Firm*—Ladas & Parry

[57] ABSTRACT

A liquid-processing apparatus for processing vital specimens, such as an automatic staining apparatus for staining specimens of vital tissues or the like for microscopic examination, has a cabinet (7) internally provided with a lower plate (8) and an upper plate (9). Rinsing vessels (10) and chemical solution vessels (11) are placed on the lower panel (8), and chemical solution vessels (11) are placed on the upper plate (9). A hanger arm (24) supporting a staining basket (13) containing glass slides carrying specimens affixed thereto moves longitudinally in a lower space (26) extending over the lower plate (8) or an upper space (28) extending over the upper plate (9). The staining basket (13) can be moved between the spaces (26, 28) through a passage (29) formed in the upper plate (9). The liquid-processing apparatus requires a small floor space for installation and can be installed in a small place. A driving unit (22) for moving the staining basket (13) needs to carry out simple operations to move the staining basket (13) only for two-dimensional motions.

21 Claims, 13 Drawing Sheets

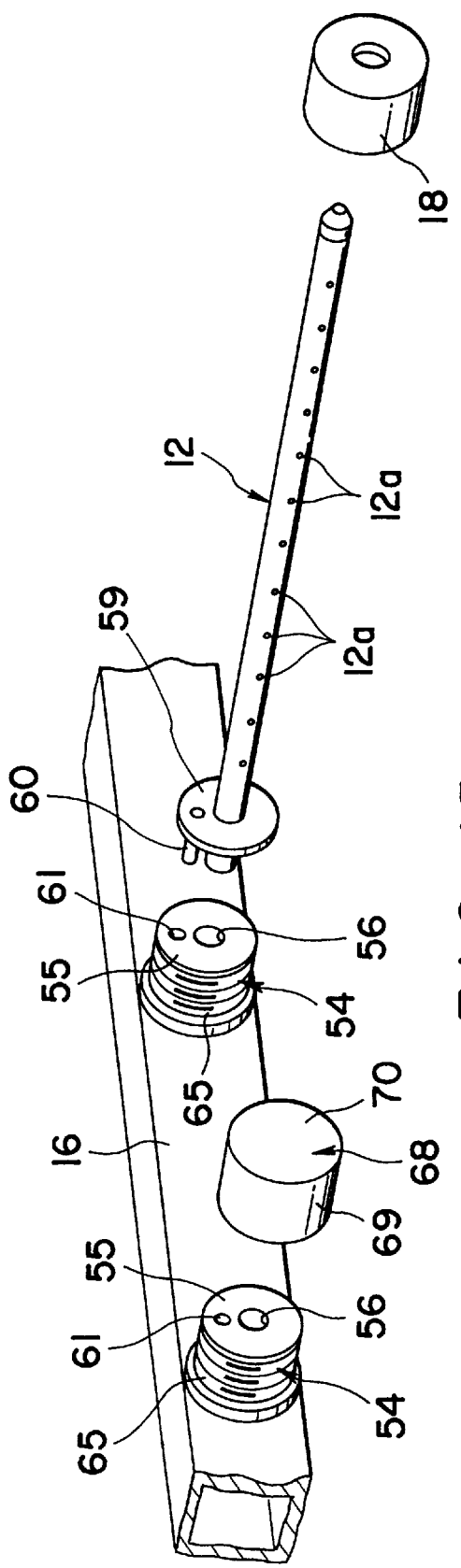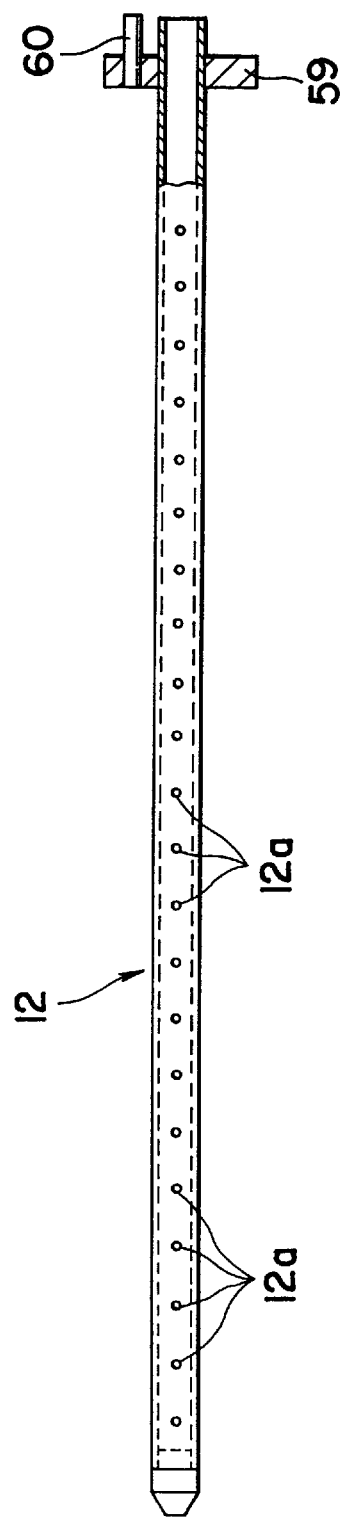
FIG. 15
FIG. 16

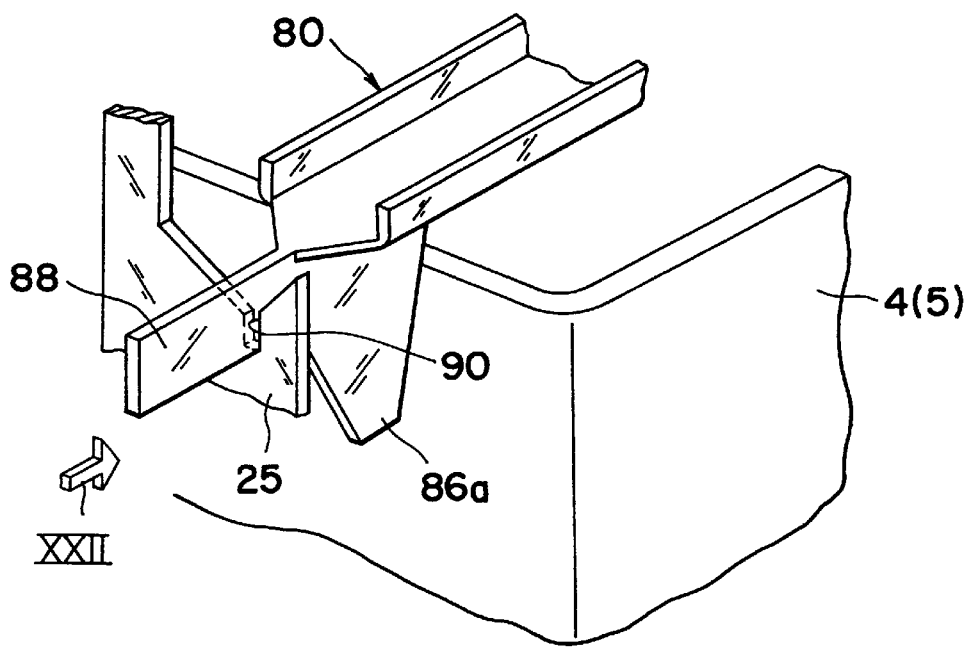
FIG. 21
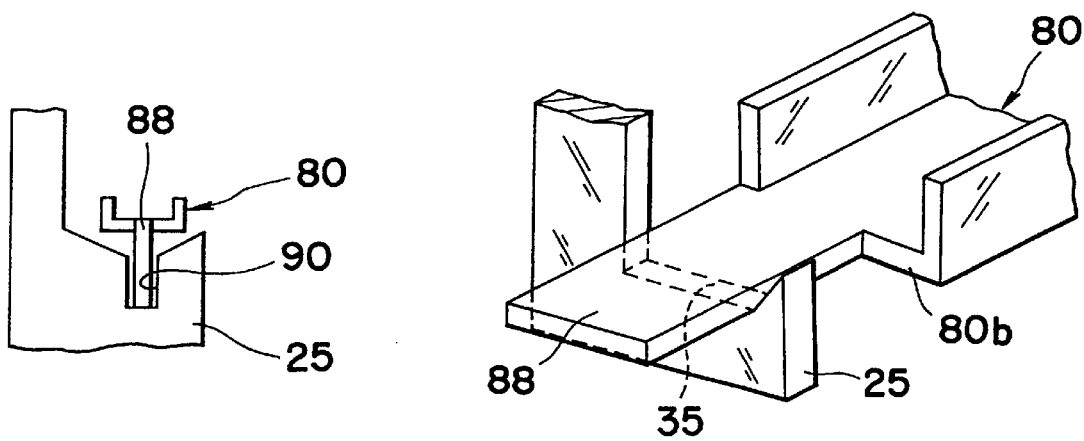
FIG. 22
FIG. 23

LIQUID TREATING APPARATUS FOR BIOLOGICAL SAMPLE

TECHNICAL FIELD

The present invention relates to a liquid-processing apparatus for processing vital specimens, biological materials such as tissues or cells of living things, (hereinafter referred to as specimens) for microscopic examination or imbedding in clinics, hospitals and research laboratories and, more particularly, to a staining apparatus.

BACKGROUND ART

In clinics and hospitals, microscopic examination of specimens sampled by excising the diseased parts is employed frequently for the diagnosis of diseases. A specimen affixed to a glass slide is stained to facilitate the diagnosis of a disease through the microscopic examination of the specimen, and various automatic staining apparatus capable of automatically staining a specimen have been proposed.

FIG. 24 shows, by way of example, an automatic staining apparatus disclosed in JP-U 5-66543A. A plurality of liquid vessels 2 respectively having open upper ends and containing chemical solutions necessary for staining processes or rinsing water are disposed in an array on a horizontal base plate in an upper section of the interior of a cabinet 1. Disposed above the liquid vessels 2 is a three-dimensional driving mechanism comprising a movable beam 3 capable of moving in a horizontal plane in longitudinal directions (in the directions of the arrows a shown in FIG. 24) with respect to the base plate, a movable column 4 capable of moving along the movable beam 3 in a horizontal plane in lateral directions (in the directions of the arrows b) with respect to the base plate, and a hanger arm 5 capable of vertically moving along the movable column 4. A staining basket capable of containing a plurality of glass slides carrying specimens affixed thereto can be detachably hung on the hanger arm 5. The hanger arm 5 supporting the staining basket is lowered to immerse the plurality of glass slides contained in the staining basket in the chemical solution or rinsing water contained in the liquid vessel 2.

When staining a specimen by using the prior art automatic staining apparatus, the staining basket containing one or more glass slides having respective specimens affixed thereto is hung on the hanger arm 5. As is generally known, the glass slides are held in a vertical attitude in the staining basket. Then, the three-dimensional driving mechanism is actuated after the staining basket has been hung on the hanger arm 5. The movable beam 3, the movable column 4 and the hanger arm 5 are moved by signals provided by a controller, not shown, to immerse the staining basket for predetermined times sequentially in the chemical solutions and the rinsing water contained in the liquid vessels 2 in a predetermined order. This operation is repeated predetermined times to stain the specimens. The automatic staining apparatus shown in FIG. 24 stores tanks 6 containing chemical solutions to be supplied to the liquid vessels 2 in a lower section of the interior of the cabinet 1 to facilitate automatic change of the frequently used chemical solutions among those contained in the liquid vessels 2. Those tanks 6 are not necessarily indispensable. An automatic staining apparatus for processing specimens for microscopic examination without the cabinet 1 for storing the tanks 6 has a height that enables the automatic staining apparatus to be installed on top of a desk, like the prior art automatic staining apparatus for processing specimens for microscopic examination disclosed in JP 6-100522B.

A prior art multiple staining process disclosed in JP 6-100522B processes a plurality of staining baskets simultaneously on an automatic staining apparatus similar to the foregoing automatic staining apparatus to stain an increased number of specimens efficiently. A staining basket containing glass slides carrying specimens affixed thereto is disengaged from the hanger arm 5 and the basket is left immersed in a chemical solution for a predetermined time, while another staining basket is hung on the hanger arm 5 to carry that next staining basket to a predetermined liquid vessel 2 and to immerse that next basket in a chemical solution contained in the predetermined liquid vessel 2 for a predetermined time. Such an operation is executed for a plurality of staining baskets for the parallel processing of specimens carried by the plurality of staining baskets. When the immersion of any of the plurality of staining baskets in the chemical solution for the predetermined time, the hanger arm 5 is brought into engagement with that staining basket to carry that staining basket to a next liquid vessel 2. Since the plurality of staining baskets can be simultaneously processed by repeating such operations, an increased number of specimens can be stained in a short time. This multiple staining process can be achieved by previously storing a procedure including those operations in the controller.

An imbedding apparatus is a liquid-processing apparatus, similar to the foregoing automatic staining apparatus, having a plurality of liquid vessels containing imbedding chemical solutions and an imbedding liquid, and carries out an imbedding process which immerses specimens sequentially in the solutions and the liquid for processing. This imbedding process is similar in principle to the staining process to be carried out by the automatic staining apparatus.

In conventional apparatus thus constructed and operated for the liquid-processing of vital specimens, the liquid vessels are arranged along a plane, so that the apparatus needs a wide area for installation, which is disadvantageous in installing the apparatus in a laboratory where only a limited area is available for installing the apparatus.

In view of this problem, the present invention provides a liquid-processing apparatus for processing vital specimens that requires a small area for installation, one capable of being easily installed in a compact laboratory space.

SUMMARY OF THE INVENTION

The present invention provides a liquid-processing apparatus for processing vital specimens, comprising a cabinet, a horizontal lower plate provided in the cabinet, a horizontal upper plate disposed in the cabinet above the lower plate and spaced from the same, a plurality of liquid vessels mounted on the lower plate, a plurality of liquid vessels mounted on the upper plate, a processing basket for containing vital specimens, a driving unit including a hanger arm for supporting the basket and for moving vertically and horizontally along the upper and the lower plate, a passage formed in a part of the upper plate in a size permitting the passage of the hanger arm supporting the basket so as to connect spaces extending respectively over and under the upper plate, and control means for controlling the driving unit to move the basket horizontally along the upper plate and the lower plate and vertically through the passage to immerse the specimens in liquids contained in the liquid vessels by immersing the basket in the liquids contained in the liquid vessels in a given order for predetermined times.

In the liquid-processing apparatus, the cabinet may have an open front side through which the liquid vessels can be taken out of the cabinet, and the open front side may be covered with an openable cover.

In the liquid-processing apparatus, it is preferable that the cover is formed in dimensions such that the cover as disposed at a position to cover the open front side of the cabinet leaves a narrow opening through which some of the liquid vessels disposed in the cabinet can be taken out of the cabinet and the liquid vessel can be put in the cabinet, and the control means is capable of setting a plurality of starting positions at which the basket is located at the start of the sequential liquid-processing operations, and a plurality of ending positions at which the basket is located at the end of the sequential liquid-processing operations.

In the liquid-processing apparatus, the cabinet has an open front side through which the liquid vessel can be taken out of the cabinet, the openable cover covers the open front side, each of support members has a sliding part extended in the direction of height of the cover, each of hinges has one end attached to a member defining the upper end of the open front side of the cabinet and the other end connected to the support member. The cover may be supported for sliding along the sliding part of the support member so that the cover is able to move backward along a top panel of the cabinet when the cover is turned on the hinges through an angle of 90° upward from the open front side of the cabinet.

The liquid-processing apparatus may comprise a rinsing liquid supply duct extended longitudinally in the space extending over the lower plate, connecting members having rinsing liquid discharge ports opening toward the front and arranged along the water supply duct, water supply pipes detachably connected to the base ends of the connecting members, caps detachably attached to the connecting members to which water supply pipes are not connected. The liquid vessels may include rinsing vessels, and each rinsing vessel may be provided with a hole in which the water supply pipe is inserted in a liquid-tight fashion when the same rinsing vessel is placed on the lower plate.

The liquid-processing apparatus may be provided with an adapter to be fixedly held on the hanger arm to support the basket. Preferably, the adapter is formed in a size large enough to support a plurality of baskets arranged side by side.

BRIEF DESCRIPTION OF THE DRAWINGS

FIG. 15 is a perspective view of a part of a water supply duct shown in FIG. 14, illustrating the steps of attaching a water supply pipe or a cap to the water supply duct;

FIG. 16 is a partly sectional side view of the water supply pipe;

FIG. 21 is a perspective view illustrating the step of placing one end of the adapter on a hook formed in a hanger arm;

FIG. 22 is a view taken in the direction of the arrow XXII in FIG. 21;

FIG. 23 is a perspective view of a support structure in a modification for supporting one end of the adapter on the hook formed in the hanger arm.

DETAILED DESCRIPTION OF THE PREFERRED EMBODIMENTS

Figure 1:
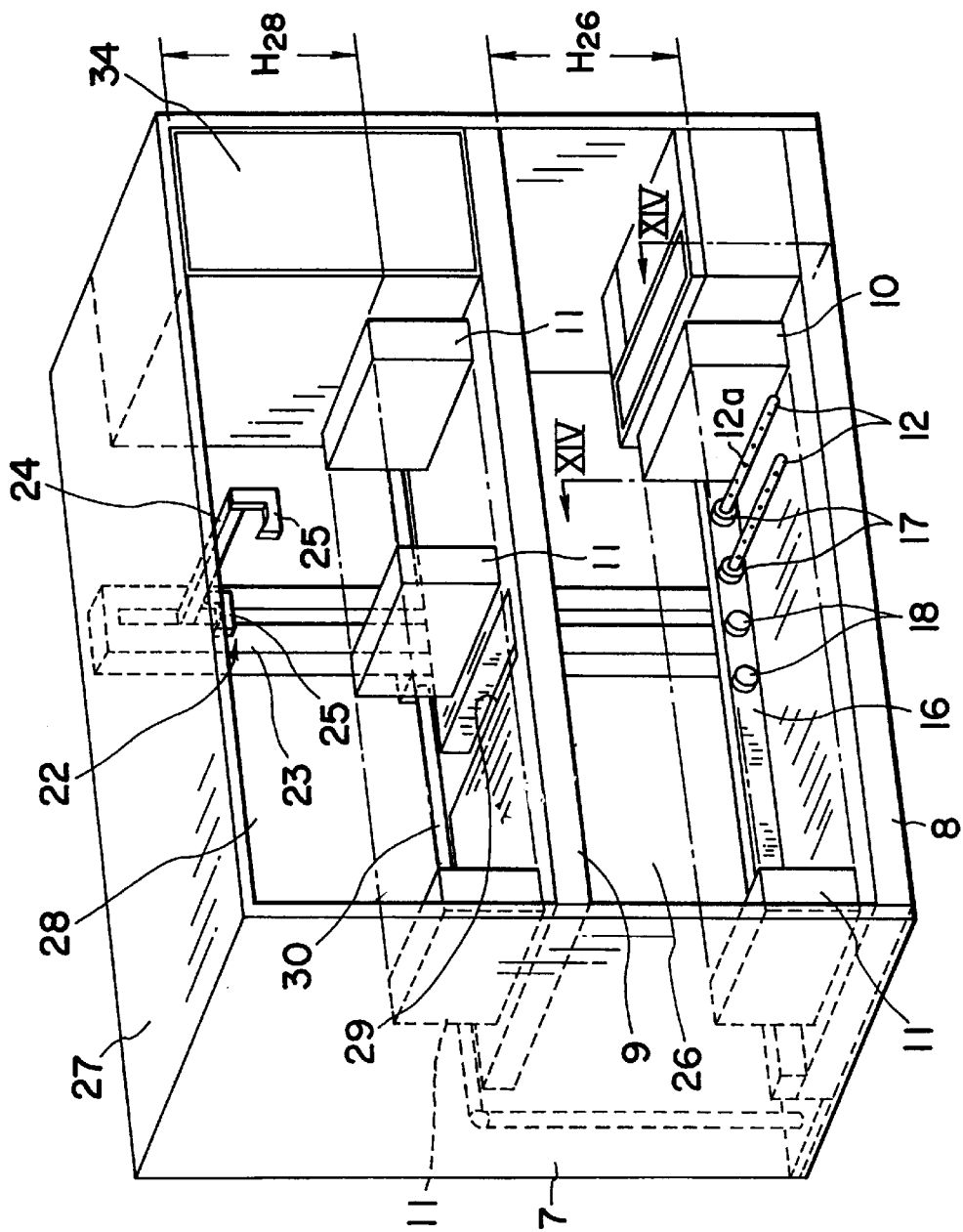
FIG. 1 is a perspective view of a liquid-processing apparatus for processing vital specimens in a preferred embodiment according to the present invention.
Figure 2:
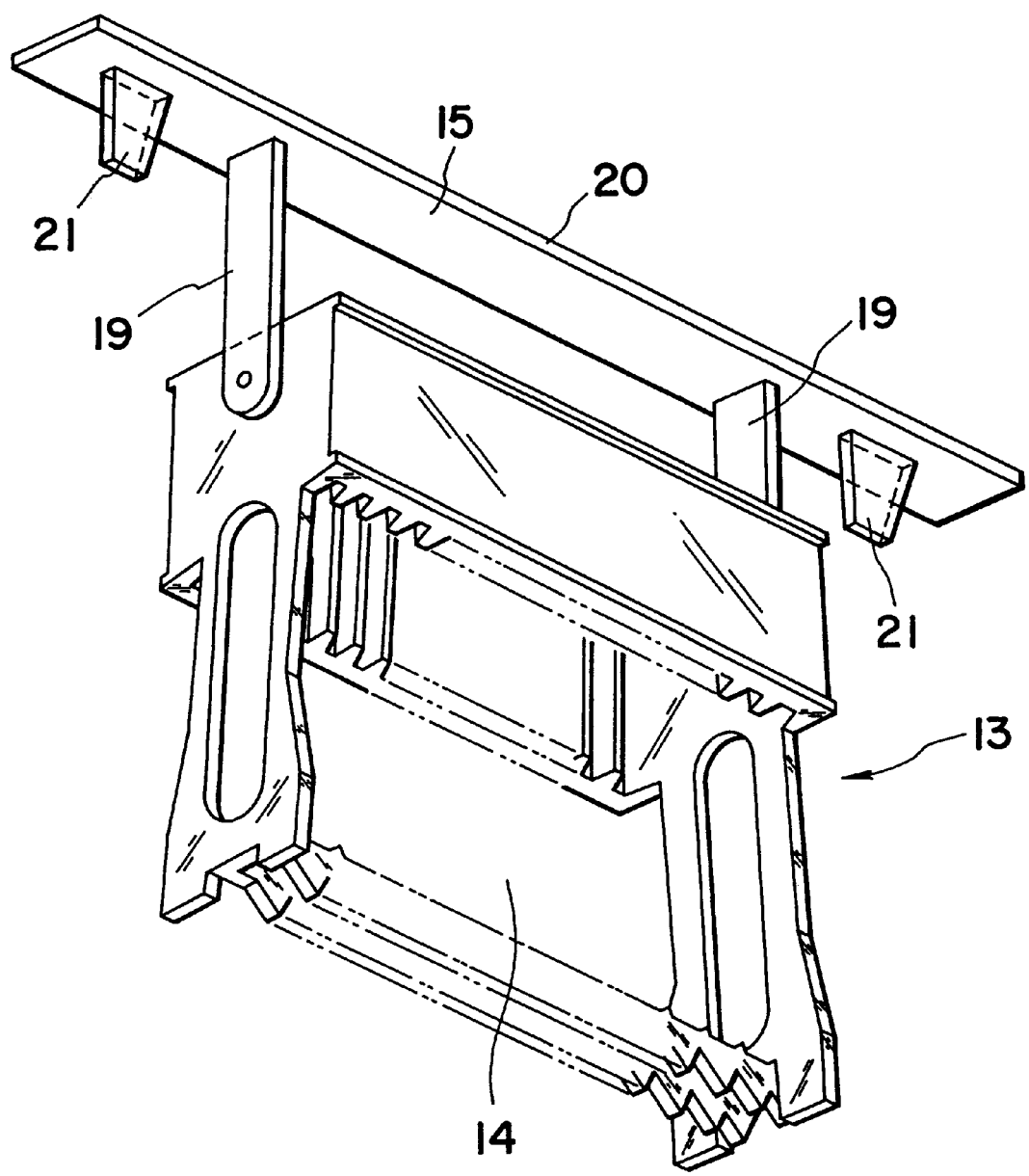
FIG. 2 is a perspective view of a staining basket employed in the liquid-processing apparatus of FIG. 1.

FIGS. 1 and 2 show a liquid-processing apparatus in a preferred embodiment according to the present invention. Specifically, the liquid-processing apparatus is an automatic staining apparatus for processing vital specimens for microscopic examination. A cabinet 7 is constructed by attaching a top panel, side panels and a back panel to a frame, and attaching a lower plate 8 to the frame so as to close an open lower surface of the frame. The cabinet 7 is a parallelepipedic structure having an open front side. An upper plate 9 is fixedly disposed in parallel to the lower plate 8 in the cabinet 7 at a middle height of the cabinet 7. A plurality of rinsing vessels 10 and a plurality of chemical solution vessels 11 are arranged on the lower plate 8 and the upper plate 9. In this embodiment, only the chemical solution vessels 11 are arranged on the upper plate 9, and the chemical solution vessels 11 and the rinsing vessels 10 are arranged on the lower plate 8. Handles are attached to the front walls of the rinsing vessels 10 and the chemical solution vessels 11 to take out the rinsing vessels 10 and the chemical solution vessels 11 from the cabinet 7 by pulling the same toward the front on the lower plate 8 and the upper plate 9, and to push the rinsing vessels 10 and the chemical solution vessels 11 into the cabinet 7 on the lower plate 8 and the upper plate 9.

A rinsing water supply pipe 12 for supplying rinsing water is inserted in a lower section of each rinsing vessel 10 through a hole, not shown, formed in a wall of the rinsing vessel 10 at a position corresponding to the rinsing water supply pipe 12. When mounting the rinsing vessel 10 on the lower plate 8, the rinsing water supply pipe 12 is inserted through the hole into the rinsing vessel 10. An 0-ring is placed between the outer circumference of the base part of the rinsing water supply pipe 12 as inserted in the rinsing vessel 10 and the inner circumference of the hole to seal the gap between the base part of the rinsing water supply pipe 12 and the rinsing vessel 10 in a liquid-tight fashion. A plurality of spouts 12a are formed in the wall of the rinsing water supply pipe 12 in a longitudinal arrangement. A staining basket 13 as shown in FIG. 2, i.e., a processing basket, is placed in the rinsing vessel 10, and then water is spouted through the spouts 12a toward a lower part of the inner surface of the rinsing vessel 10 to generate water currents. Each of the chemical solution vessels 11 contains a chemical solution for staining specimens affixed to glass slides contained in the staining basket 13.

The rinsing water supply pipes 12 are extended in a horizontal direction and detachably fixed with a coupling nut 17 to the front wall of a water supply duct 16 disposed on a back part of the lower plate 8 and connected to a water supply system. A plurality of pipe fittings (five pipe fittings in the embodiment) are attached to the front wall of the water supply duct 16, and the base ends of the water supply pipes 12 are detachably coupled with the pipe fittings. Caps 18 similar to cap nuts are put on pipe fittings not coupled with the water supply pipes 12, and the chemical solution vessels 11 are disposed in front of the those pipe fittings. Water spouted from the water supply pipe 12 into the rinsing vessel 10 fills up the rinsing vessel 10, overflows the rinsing vessel 10 onto the lower plate, and is drained through a drain pipe into a drainage system.

Referring to FIG. 2, the staining basket 13, i.e., processing basket, has a glass slide holding unit 14, and a handle unit 15 pivotally connected to an upper part of the glass slide holding unit 14. As is generally known, the glass slide holding unit 14 is capable of holding a plurality of glass slides in a vertical attitude with a space between adjacent glass slides. The glass slide holding unit 14 is a frame capable of holding glass slides and of being immersed in a liquid contained in a vessel to immerse the glass slide held thereon in the liquid. The handle unit 15 has arms 19 each having one end pivotally connected to an upper part of a side wall of the glass slide holding unit 14, and a support beam 20 connected to the upper ends of the arms 19. The opposite end parts of the support beam 20 extend beyond parts corresponding to the opposite longitudinal ends of the glass slide holding unit 14. Projections 21 are projected from the lower surfaces of the opposite end parts of the support beam 20.

When inserting glass slides in the glass slide holding unit of the staining basket 13, the arms 19 are turned relative to the glass slide holding unit 14 to move the support beam 20 away from a support position above the open upper end of the glass slide holding unit 14. When subjecting specimens to a staining process, the support beam 20 is moved to the support position above the open upper end of the glass slide holding unit 14 as shown in FIG. 2 after glass slides carrying the specimens affixed thereto have been inserted in the glass slide holding unit 14.

A driving unit 22 is installed in the cabinet 7 to move the staining basket 13 vertically and horizontally in the cabinet 7. In this embodiment, the driving unit 22 comprises a movable column 23 capable of horizontally moving along a longitudinal guide rail 30 installed in a back section of the cabinet 7, and a hanger arm 24 capable of vertically moving along the movable column 23. Drive mechanisms for horizontally moving the movable column 23 and for vertically moving the hanger arm 24 may be known ones. For example, each of the drive mechanisms may be a linear motor, or a cable drive mechanism comprising a drive pulley, a driven pulley, and a cable wound around the drive pulley and the driven pulley and fixed to the movable column 23 or the hanger arm 24. The cable drive mechanism is particularly preferable because an electric motor included in the cable drive mechanism can be disposed at a position where the electric motor may not be exposed to the vapor of a chemical solution produced in the chemical solution vessel. The driving unit 22 moves either the movable column 23 or the hanger arm 24 or both the movable column 23 and the hanger arm 24 to immerse the staining basket 13 in the chemical solutions and the rinsing water contained in the chemical solution vessels 11 and the rinsing vessels 10 placed on the lower plate 8 and the upper plate 9 for predetermined times in a predetermined order. Thus, the specimens affixed to the glass slides contained in the staining basket 13 are immersed in the chemical solution contained in the chemical solution vessel 11 or the rinsing water contained in the rinsing vessel 10 to stain the specimens. Conditions for the immersion process including operations to be carried out in a predetermined order can be optionally set by operating a control panel placed on the front side of an immersion process control unit 34.

The hanger arm 24 is provided at its front and back ends with hooks 25 on which the support beam 20 of the staining basket 13 is hung. When hanging the staining basket 13 on the hanger arm 24, the hanger arm 24 is moved to a position under the support beam 20 so that the hooks 25 are on the outer side of the projections 21 of the support beam 20, and then the hanger arm 24 is raised to support the staining basket 13. These operations are reversed to separate the hanger arm 24 from the staining basket 13.

A lower space 26 is secured between the upper ends of the rinsing vessels 10 and the chemical solution vessels 11 placed on the lower plate 8, and the lower surface of the upper plate 9 to enable the staining basket 13 to be put in the chemical solution vessels 11 and the rinsing vessels 10 placed on the lower plate 8. The height $H_{26}$ of the lower space 26 is sufficient for the hanger arm 24 supporting the staining basket 13 to move longitudinally without making a lower part of the staining basket 13 collide against the upper ends of the vessels 10 and 11. An upper space 28 is secured between the upper ends of the chemical solution vessels 11 placed on the upper plate 9, and the lower surface of a top panel 27 of the cabinet 7. The height $H_{28}$ of the upper space 28 is sufficient for the hanger arm 24 supporting the staining basket 13 to move longitudinally without making a lower part of the staining basket 13 collide against the upper ends of the vessels 10 and 11. A passage 29 of, for example, a rectangular shape large enough to move the hanger arm 24 supporting the staining basket 13 therethrough is formed in a middle part of the upper plate 9.

The specimens affixed to the glass slides contained in the staining basket 13 are stained by the liquid-processing apparatus thus constructed according to the present invention by the following staining procedure. First the staining basket 13 containing the glass slides is hung on the hanger arm 24 by, for example, placing the staining basket 13 in one of the rinsing vessels 10 and moving the hanger arm 24 to a position above the staining basket 13. Then, the movable column 23 and the hanger arm 24 of the driving unit are moved properly to immerse the staining basket 13 for predetermined times in the chemical solutions contained in the chemical solution vessels 11 or the rinsing water contained in the rinsing vessels 10 in a predetermined order. A staining cycle including these operations is repeated a predetermined number of times to stain the specimens.

The hanger arm 24 is moved longitudinally in the lower space 26 or the upper space 28, and is moved vertically above a predetermined rinsing vessel 10 or a chemical solution vessel 11 to immerse the staining basket 13 in the rinsing water contained in the rinsing vessel 10 placed on the lower plate 8, in the chemical solution contained in the chemical solution vessel 11 placed on the lower plate 8 or in the chemical solution contained in the chemical solution vessel 11 placed on the upper plate 9. During the staining process, the staining basket 13 needs to be transferred from the chemical solution contained in a chemical solution vessel 11 placed on the upper plate 9 to the rinsing water contained in a rinsing vessel 10 placed on the lower plate 8 or to the chemical solution contained in a chemical solution vessel 11 placed on the lower plate 8, or from the rinsing water contained in the rinsing vessel 10 placed on the lower plate 8 or the chemical solution contained in the chemical solution vessel 11 placed on the lower plate 8 to the chemical solution contained in the chemical solution vessel 11 placed on the upper plate 9, and the hanger arm 24 supporting the staining basket 13 moves through the passage 29 formed in a middle part of the upper plate 9 between the lower space 26 and the upper space 28.

When simultaneously subjecting a plurality of staining baskets 13 to the same staining processes or to different staining processes, the hanger arm 24 is separated from the staining basket 13 after putting the staining basket 13 in a rinsing vessel 10 or a chemical solution vessel 11, and another staining basket 13 is carried by the hanger arm 24. The hanger arm 24 is shook vertically in a small amplitude before separating the hanger arm 24 from the staining basket 13 to vibrate the staining basket 13 in the rinsing water or the chemical solution in order that the specimens affixed to the glass slides contained in the staining basket 13 are wetted uniformly with the rinsing water or the chemical solution. The process control unit 34 can be arranged for the random access of the staining basket 13 to the rinsing vessels 10 and the chemical solution vessels 11.

In this embodiment, the upper plate 9 is fastened to the frame of the cabinet 7, and the lower space 26 and the upper space 28 are formed respectively in heights $H_{26}$ and $H_{28}$ sufficient for the hanger arm 24 supporting the staining basket 13 to move longitudinally without making a lower part of the staining basket 13 collide against the upper ends of the vessels 10 and 11. The upper plate 9 may be supported on the frame of the cabinet so as to be vertically movable in a horizontal attitude. The automatic staining apparatus can be formed in a small overall height by supporting the upper plate 9 on the frame so as to be vertically movable in the horizontal attitude, and the height of the upper space 28 is increased by lowering the upper plate 9 (the height of the lower space 26 is reduced) after moving the hanger arm 24 supporting the staining basket 13 through the passage 29 to a position above the upper plate 9.

The vessels including the rinsing vessels 10 and the chemical solution vessels 11 may be arranged in three or more tiers. At least one intermediate plate, not shown, provided with a passage 29 similar to that of the upper plate 9 is placed between the lower plate 8 and the upper plate 9 and some of the chemical solution vessels 11 are placed on the intermediate plate. The lower space 26 is formed between the upper ends of the rinsing vessels 10 and the chemical solution vessels 11 placed on the lower plate 8, and the lower surface of the intermediate plate. An intermediate space sufficient for the hanger arm 24 supporting the staining basket 13 to move longitudinally therein is secured between the upper ends of the chemical solution vessels 11 placed on the intermediate plate, and the lower surface of the upper plate 9.

The automatic staining apparatus can be formed in a smaller overall height by supporting the intermediate plate on the frame so as to be vertically movable in the horizontal attitude, and the height of the intermediate space is increased by lowering the intermediate plate after moving the hanger arm 24 supporting the staining basket 13 through the passage 29 to a position above the intermediate plate.

In either of the foregoing structures, the passages 29 of the upper plate 9 and the intermediate plate may be formed in longitudinal end parts of the upper plate 9 and the intermediate plate instead of in the middle parts of the same. If the passage 29 is formed in a region above the rinsing vessel 10 placed on the lower plate 8, the chemical solution wetting the staining basket 13 and the glass slides contained in the staining basket 13 is caused to drip into the rinsing vessel 10 and does not drip into the chemical solution vessels 11 containing other chemical solutions when the hanger arm 24 supporting the staining basket 13 moves vertically through the passage 29 and hence the other chemical solutions will not be deteriorated. Since fresh rinsing water is supplied continuously through the water supply pipe 12 into the rinsing vessel 10 and the rinsing water contained in the rinsing vessel 10 is replaced continuously with fresh rinsing water, drops of the chemical solution dripped into the rinsing vessel 10 cause problems scarcely. An empty vessel may be disposed instead of the rinsing vessel 10 below the passage 29 to contain the chemical solution dripped from the staining basket 13 and the glass slides contained in the staining basket 13.

The automatic staining apparatus may be provided with a plurality of sets of the movable column 23 and the hanger arm 24, and the movable columns 23 and the hanger arms 24 may be assigned to operations in the right-hand sections and the left-hand sections of the spaces, respectively, to achieve the simultaneous handling of the plurality of staining baskets smoothly and properly.

The liquid-processing apparatus for processing specimens for microscopic examination has the foregoing configuration and carries out the foregoing operations. Therefore, the liquid-processing apparatus does not need a large floor space for installation and can be installed in a small test room. Thus the liquid-processing apparatus can be installed in clinics, hospitals and research laboratories of a small scale in which it has been difficult to install conventional liquid-processing apparatus.

If a plurality of vessels need to be arranged in the conventional liquid-processing apparatus in which the vessels can be arranged only in a single tier, the vessels need to be arranged in a plurality of rows arranged in the lateral direction of the liquid-processing apparatus to form the liquid-processing apparatus to have a limited width. In such a conventional liquid-processing apparatus, the driving unit for moving a glass slide basket must be capable of moving the glass slide basket in vertical directions, longitudinal directions and lateral directions in a three-dimensional space. According to the present invention, the liquid-processing apparatus can be provided with an increased number of vessels, and the glass slide basket needs to be moved only in vertical directions and longitudinal directions in a virtually two-dimensional space and hence the driving unit may be of a simple mechanism. If the glass slide basket can be kept at a standby position in a vertical plane including the vertical passage, work for handling the vessels will not be obstructed by the hanger arm and the hanger arm need not be moved by hand when taking out the vessel from and when putting the vessel into the liquid-processing apparatus.

Figure 3:
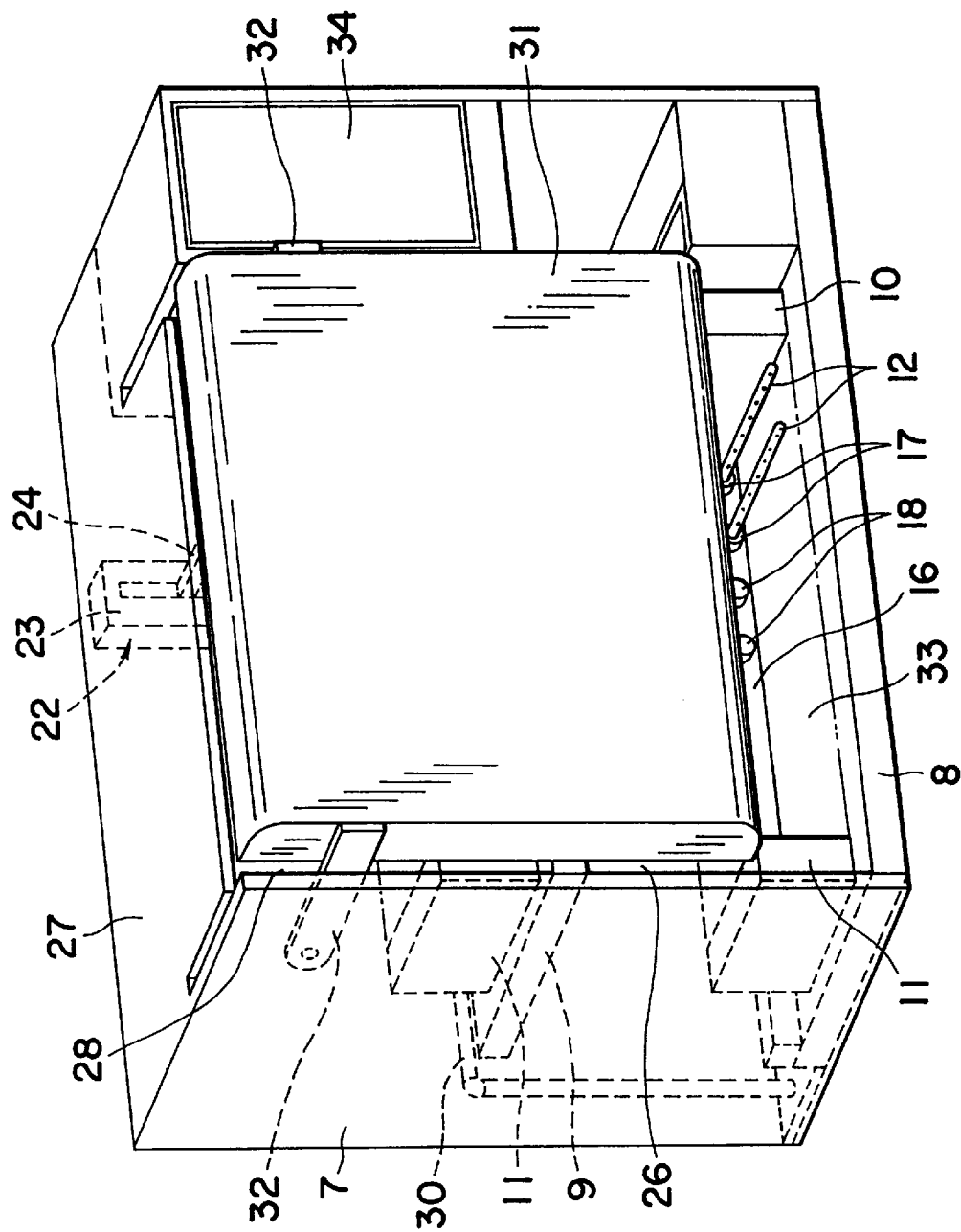
FIG. 3 is a perspective view of the embodiment shown in FIG. 1 provided with a cover on its front side.
Figure 4:
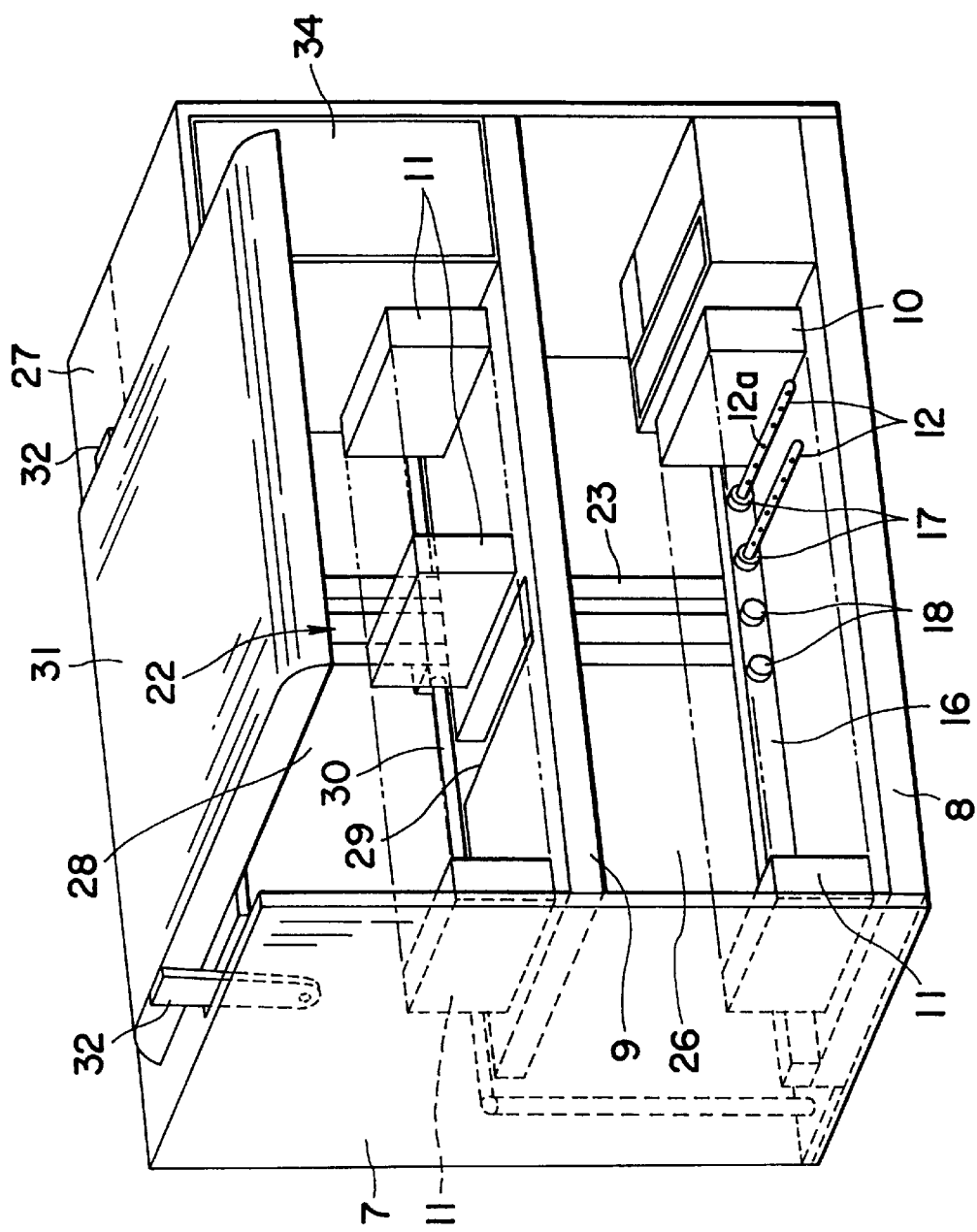
FIG. 4 is a perspective view of the embodiment shown in FIG. 3 in a state where the cover is opened.

The cabinet 7 provided with the mechanisms for carrying out the staining process has an open front side covered with an openable cover 31 as shown in FIGS. 3 and 4. The cover 31 is formed from a semitransparent acrylic resin plate or the like. A pair of swing arms 32 are attached to the cover 31 and are pivotally supported on upper parts of the cabinet 7 so that the cover 31 can be turned to a position above the cabinet 7. When the cover 31 is lowered to its lower position, the open front side of the cabinet 7 excluding a lower end section is covered with the cover 31. Even in a state where the cover 31 is lowered to its lower position, a narrow opening 33 is formed under the cover 31, the opening 33 being large enough to take out the rinsing vessels 10 and the chemical solution vessels 11 placed on the lower plate 8 and to put the rinsing vessels 10 and the chemical solution vessels 11 on the lower plate 8. Therefore, the rinsing vessels 10 and the chemical solution vessels 11 placed on the lower plate 8 are replaceable with the cover 31 positioned at its lower position to cover the open front side of the cabinet 7. In a state where the cover 31 is raised to its upper position as shown in FIG. 4, the rinsing vessels 10 and the chemical solution vessels 11 placed on the upper plate 9 as well as those placed on the lower plate 8 are replaceable. If necessary, the narrow opening 33 may be covered with another openable cover. As mentioned above, it is desirable that the vessels 10 and 11 are provided with handles on their front walls to facilitate work for replacing the vessels 10 and 11. If the vessels 10 and 11 are provided with handles on their front walls, the vessels 10 and 11 need not be provided with handles at upper parts thereof and the vessels 10 and 11 can be arranged at small pitches.

In this liquid-processing apparatus for processing specimens for microscopic examination, the vessel in which the staining basket 13 is put in the first step among the sequential steps of the staining process and the vessel in which the staining basket 13 is put in the last step among the sequential steps of the staining process can be selected out of the rinsing vessels 10 and the chemical solution vessels 11 placed on the lower plate 8 by operating switches and keys, not shown, arranged on the front panel of the process control unit 34.

In the embodiment shown in FIGS. 3 and 4, the staining basket 13 is put in the vessel placed at a position where the staining basket 13 is to be placed at the completion of the staining process after the staining process has been completed. Then, the vessel containing the staining basket 13 which has undergone all the steps of the staining process is taken out of the cabinet through the narrow opening 33. In this liquid-processing apparatus, each of a position where the basket 13 is placed at the start of the liquid-processing process and a position where the basket 13 is placed at the end of the liquid-processing process can be optionally selected out of a plurality of positions corresponding to the plurality of rinsing vessels 10 and the plurality of chemical solution vessels 11 placed on the lower plate 8, which facilitate the liquid-processing of the specimens affixed to the glass slides contained in the plurality of baskets 13; that is, the operator need not position a succeeding basket 13 before the hanger arm 24 which has moved the preceding basket 13 to another position returns or need not take out the preceding basket 13 which has undergone all the steps of the liquid-processing process before the succeeding basket 13 is carried to a position where the basket 13 is to be taken out.

Figure 5:
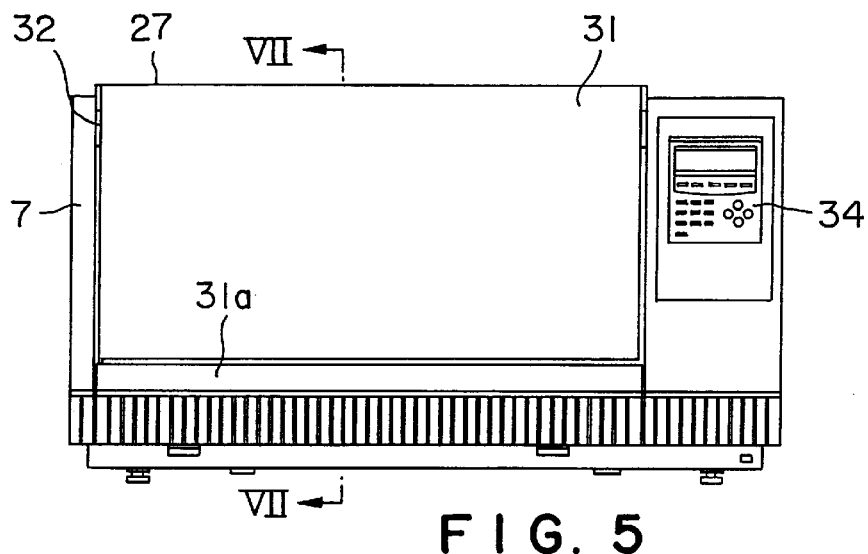
FIG. 5 is a front view of a commercial model of the liquid-processing apparatus shown in FIG. 3.
Figure 6:
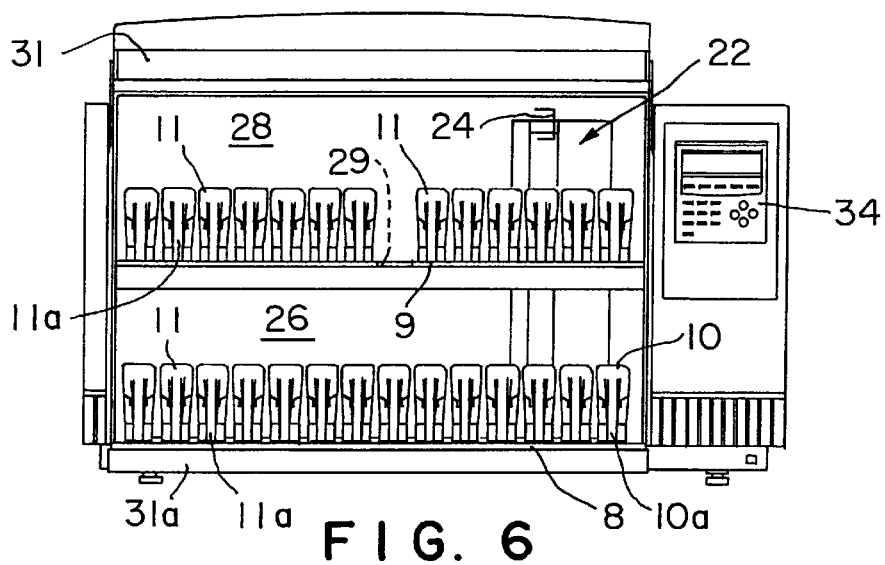
FIG. 6 is a front view of the commercial model of the liquid-processing apparatus shown in FIG. 5 in a state where a cover is opened.
Figure 7:
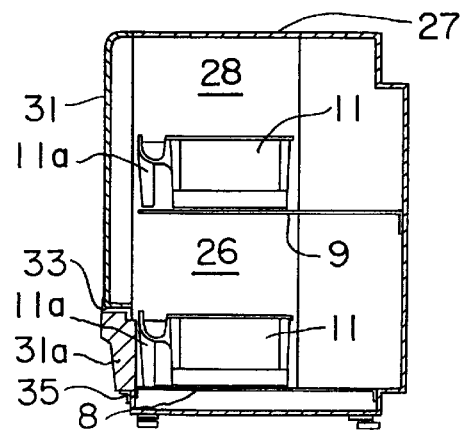
FIG. 7 is a sectional view taken on line VII—VII in FIG. 5.

FIGS. 5 to 7 show the liquid-processing apparatus shown in FIGS. 3 and 4 in a commercial model. As shown in FIG. 5, an open front side of a cabinet 7 is covered with an openable cover 31. In a state where the cover 31 is moved to an upper position above a top panel 27 to open the open front side as shown in FIG. 6, chemical solution vessels 11 are placed on the entire surface of an upper plate 9 excluding a part of the surface corresponding to a passage 29. Normally, a narrow opening 33 under the cover 31 is covered with a lower door 31a as shown in a sectional view in FIG. 7. The lower door 31a is turned on hinges 35 attached to its lower edge toward the front to open the narrow opening 33 only when taking out the vessels 10 and 11. The lower door 31a improves the external design of the liquid-processing apparatus. The vessels 10 and 11 are provided on their front wall with handles 10a and 11a, respectively, to facilitate work for taking out the vessels 10 and 11.

The cover 31 of a flip-up type shown in FIGS. 3 and 4 needs a space of a thickness corresponding to the height of the cover 31 over the cabinet 7 and a large space in front of the cabinet 7. Therefore, the liquid-processing apparatus needs a large three-dimensional space for installation and therefore the liquid-processing apparatus is subjected to a limitation to the installation space. If the liquid-processing apparatus is provided with a pair of swing doors, which open sidewise, the liquid-processing apparatus also needs large spaces for the swing motion of the doors in front of and beside the cabinet.

Figure 8:
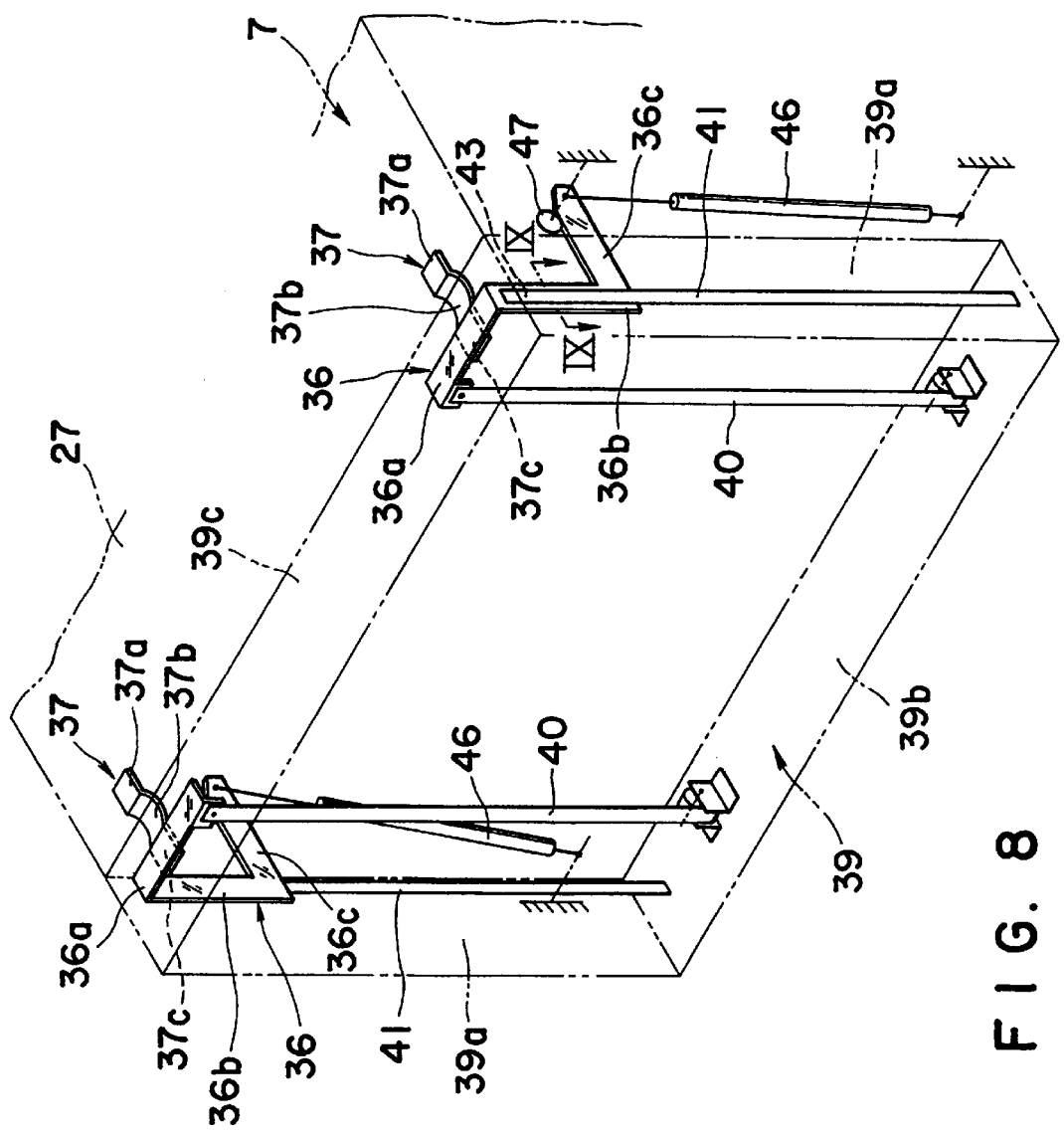
FIG. 8 is a perspective view of a cover of another type disposed on the front side of the liquid-processing apparatus, and support members supporting the cover.

FIGS. 8 to 13 show an embodiment capable of solving such problems. Referring to FIG. 8, support members 36 are supported on plate hinges 37 made from an elastic metal strip and attached to the lower surface of a top panel 27 defining the upper end of the open front side of a cabinet 7. Each of the plate hinges 37 has a first end part 37a attached to the lower surface of the top panel 27, a second end part 37c attached to a horizontal part 36a of the support member 36 by welding or the like, and a downward convex curved middle part 37b connecting the first end part 37a and the second end part 37c. The curved middle part 37b is capable of elastic deformation. The support members 36 are held on the inner surface, i.e., the lower surface, of a top wall of a cover 39, and hence the support members 36 are concealed from view to avoid spoiling the appearance of the cabinet.

A constant-load spring 40, i.e., a spiral spring formed by winding a flexible metal strip, has one end fastened to the inner surface of a lower wall 39b of the cover 39, and the other end connected to the horizontal part 36a of the support member 36. A coil spring whose resilience varies may be employed as the spring 40 instead of the spiral spring. A slide block 43 which slides along a guide rail 41 (FIG. 9) fixed to the inner surface of a side wall 39a of the cover 39 is attached to a sliding part 36b of the support member 36. An arm part 36c extends backward from the lower end of the sliding part 36b. A gas damper 46 has one end connected to the arm part 36c and the other end connected to the cabinet 7. The gas damper 46 exerts pressure to the arm part 36c by the pressure of a gas sealed therein. A stopper 47 is attached to the inner surface of a side wall of the cabinet 7. When the cover 39 is closed, the arm part 36c comes into contact with the stopper 47 to stop the cover 39 at a predetermined position. The stopper 47 may be a block of an abrasion-resistant material or a roller. If the cover 39 has a small weight and the pressure of the gas damper 46 is low, the stopper may be omitted. Two sets of the plate hinge 37, the support member 36, the constant-load spring 40 and the gas damper 46 are disposed on the opposite sides of the cover 39, respectively. If the cover 39 is light and sufficiently rigid, only one set of the plate hinge 37, the support member 36, the constant-load spring 40 and the gas damper 46 may be disposed on one side of the cover 39.

The cover 39 thus covering the open front side of the cabinet 7 is opened and closed by the following operations.

Figure 10:
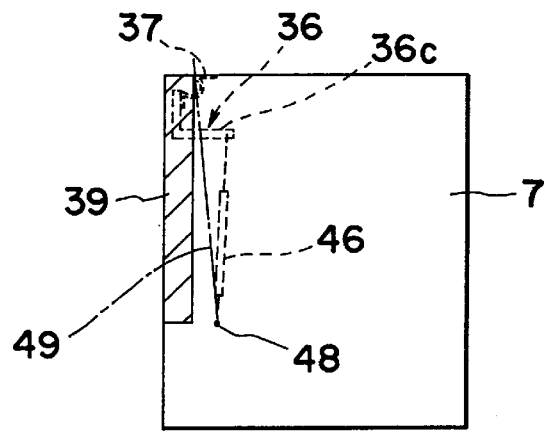
FIG. 10 is a schematic side view of an arrangement shown in FIG. 8 in a state where the cover is closed.

While the cover 39 is at a closed position to close the open front side of the cabinet 7, each of the support members 36 is in a state shown in FIGS. 8 and 10, in which the gas damper 46 exerts pressure on the arm part 36c of the support member 36 to keep the cover 39 closed. Since the cover 39 is not very heavy and the resilience of the constant-load spring 40 need not be very high, the cover 39 can be kept closed by the gas damper 46. If it is desired that the resilience of the constant-load spring 40 is high enough to raise the cover 39, the cover 39 may be locked in place on the cabinet 7 by a locking device provided on an ordinary cover.

Figure 11:
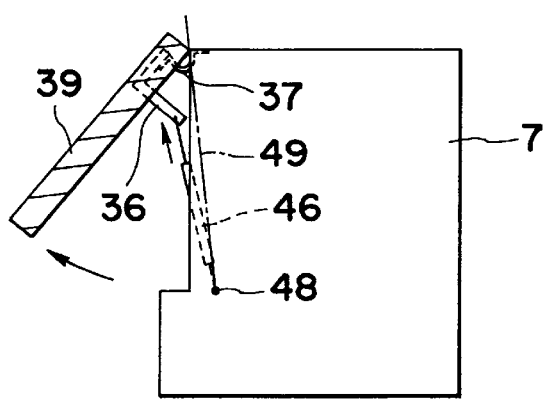
FIG. 11 is a schematic side view of the arrangement shown in FIG. 8 in a state where the cover is slightly opened.
Figure 12:
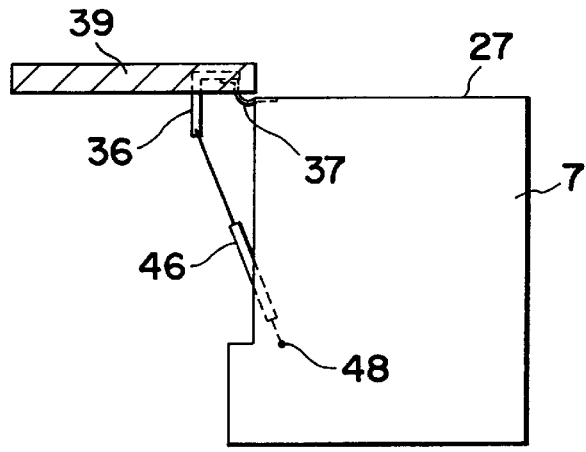
FIG. 12 is a schematic side view of the arrangement shown in FIG. 8 in a state where the cover is fully opened.

When opening the cover 39, a lower part of the cover 39 is pulled slightly toward the front as shown in FIG. 11. After the joint of the arm part 36c and the gas damper 46 has moved toward the front beyond a line 49 connecting the joint 48 of the gas damper 46 and the cabinet 7 and the center of turning of the curved part 37b of the plate hinge 37, the pressure of the gas damper 46 acts to push up the cover 39. In this state, the cover 39 is held by hand to restrain the cover 39 from being raised by the resilience of the constant-load spring 40.

Figure 13:
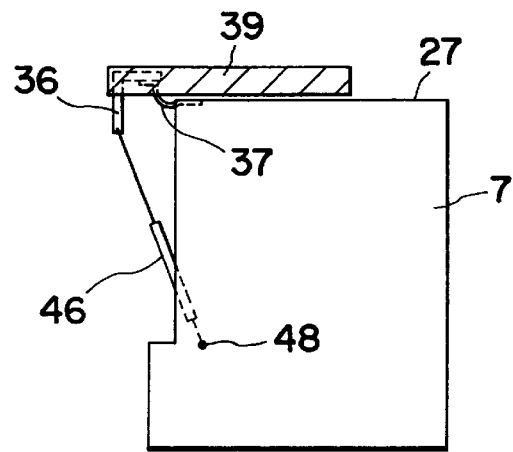
FIG. 13 is a schematic side view of the arrangement shown in FIG. 8 in a state where the cover is moved to a position above a cabinet.

Then, the cover 39 is further opened until the cover 39 extends in parallel to the top panel 27. Since the pressure of the gas damper 46 acts upward on the cover 39, the cover 39 will not move down suddenly even if the cover 39 is let go. Since the constant-load spring 40 pulls the cover 39 toward the back of the cabinet 7 in parallel to the top panel 27, the slide blocks 43 attached to the sliding parts 36b of the support members 36 slide along the guide rails 41, so that the cover 39 is pulled backward along the top panel 27 as shown in FIG. 13. If the resilience biasing the cover 39 backward is insufficient, the cover 39 is pushed backward by hand.

When closing the cover 39, the foregoing operations are reversed. The resilience of the constant-load springs 40 and the pushing force of the gas dampers 46 are adjusted properly so that the cover 39 can be opened and closed by applying a small force to the cover 39 by hand or by scarcely applying force to the cover 39.

Figure 9:
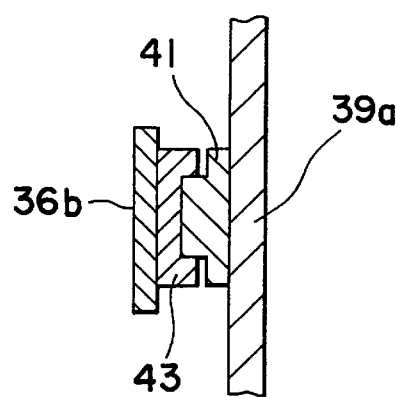
FIG. 9 is an enlarged sectional view taken on line IX—IX in FIG. 8.

The guide mechanisms each comprising the guide rail 41 and the slide block 43 shown in FIG. 9 may be replaced with rack-and-pinion guide mechanisms each comprising a rack and a pinion. If a rack-and-pinion guide mechanism is employed, the rack is provided on the side wall 39a of the cover, the pinion is supported on the sliding part 36b, and the action of a rotary damper equivalent in function to the constant-load spring 40 is exerted on the pinion.

Since the resiliences of the constant-load springs or the like and the gas dampers are exerted on the cover, the cover can be lightly opened and closed only by applying a force to the cover by hand.

A wide space need not be secured over the cabinet for the cover because the cover moves along the cabinet when the same is opened and is held over the cabinet in parallel to the upper surface of the cabinet. Therefore, only a space of a height slightly greater than the thickness of the cover needs to be secured over the cabinet.

Even if the cover tends to fall down by its own weight while the cover is opened or closed, the cover is restrained from sudden drop or from falling by the resiliences of the constant-load springs and the gas dampers. Therefore there is no possibility that the operator is injured or laboratory instruments and implements are damaged.

Since the resiliences of the constant-load springs and the gas dampers may be on the order of a magnitude sufficient to supplement a force applied to the cover by hand to move the same, the cover can be lightly and surely operated by hand.

Since the opened cover is stored over the cabinet, there is no obstruct on the front side of the liquid-processing apparatus, the liquid-processing apparatus is easy to use and the liquid-processing apparatus can be built in a good design.

Figure 24:
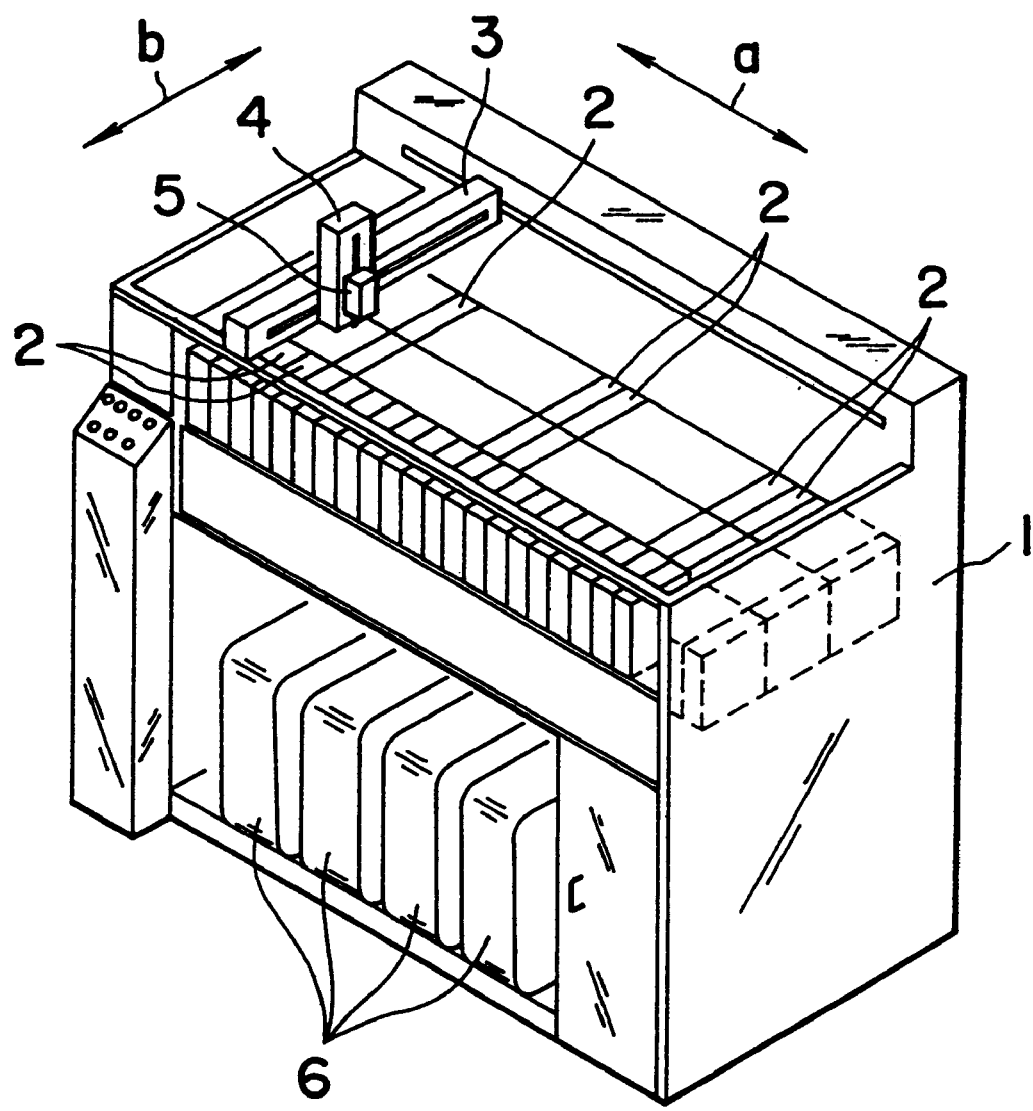
FIG. 24 is a perspective view of a conventional staining apparatus.

In the prior art automatic staining apparatus for preparing specimens for microscopic examination shown in FIG. 24, the number of the liquid vessels 2 to be used as rinsing vessels among the liquid vessels 2 is fixed. Rinsing water supply pipes need to be disposed in the bottoms of the liquid vessels 2 to be used as rinsing vessels, and, in the prior art automatic staining apparatus, those pipes are disposed at predetermined fixed positions. Therefore, liquid vessels 2 to be used as rinsing vessels can be disposed only at positions corresponding to the pipes and cannot be disposed at positions other than those corresponding to the pipes.

Since the number of liquid vessels 2 which can be used as rinsing vessels is fixed, the prior art automatic staining apparatus is incapable of changing the number of the liquid vessels 2 to be used as rinsing vessels when the staining method is changed and the number of the liquid vessels 2 to be used as rinsing vessels needs to be changed accordingly. It is preferable, to carry out a staining process smoothly, that the number of the liquid vessels 2 to be used as rinsing vessels is changed and the number of liquid vessels 2 to be used as chemical solution vessels is changed accordingly when the staining method is changed.

Such a problem can be solved by structures associated with the pipes 12 shown in FIG. 1. The structures will be described hereinafter with reference to FIGS. 14 to 18.

Figure 14:
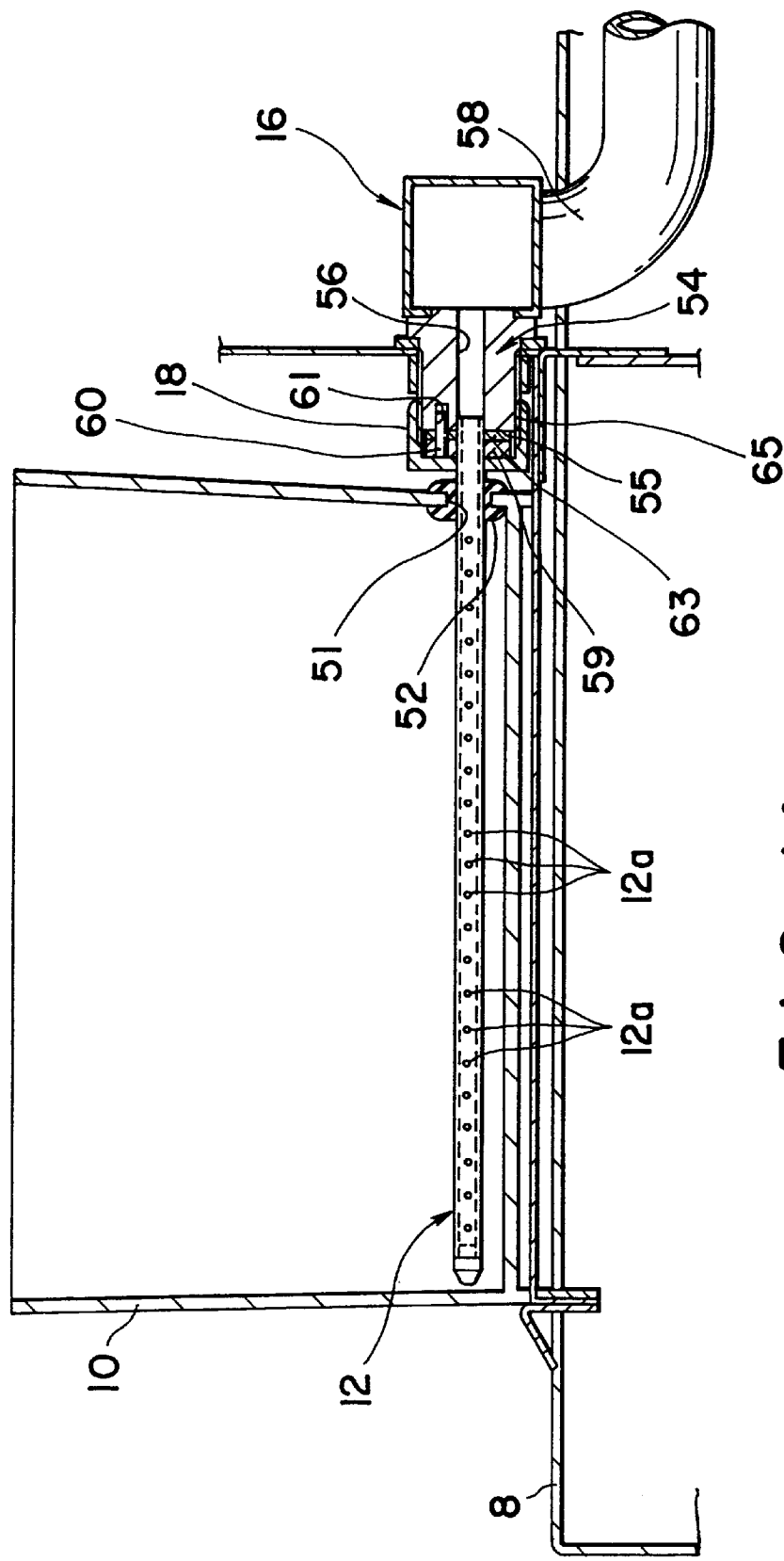
FIG. 14 is a sectional view taken on line XIV—XIV in FIG. 1.
Figure 17:
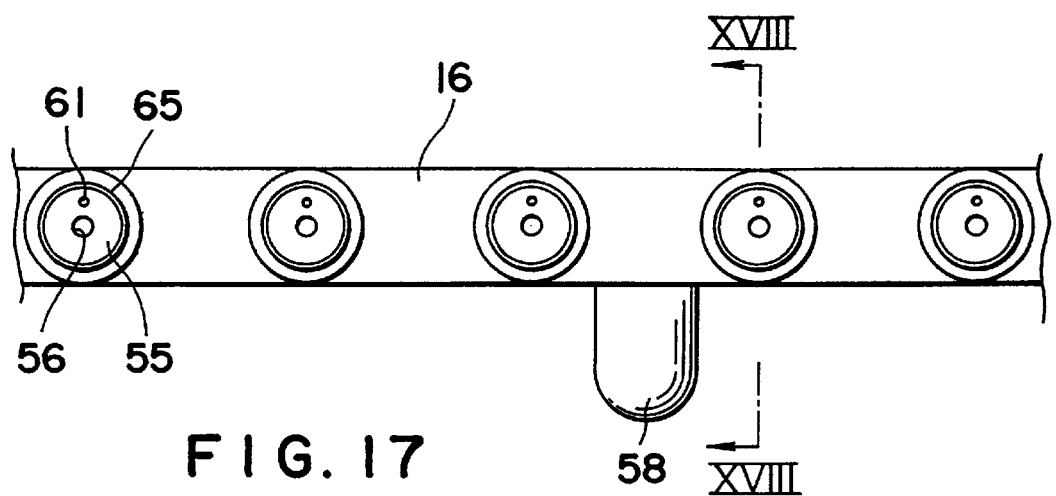
FIG. 17 is a front view of the water supply duct.
Figure 18:
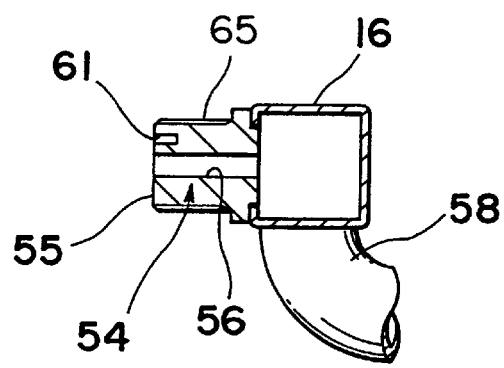
FIG. 18 is a sectional view taken on line XVIII—XVIII in FIG. 14.

Referring to FIG. 14 showing a sectional view taken on line XIV—XIV in FIG. 1, the rinsing water supply pipe 12 for supplying rinsing water is inserted in a lower part of the rinsing vessel 10. An opening 51 is formed in the back wall of the rinsing vessel 10 at a position corresponding to the rinsing water supply pipe 12. The rinsing water supply pipe 12 can be inserted in and taken out from the rinsing vessel 10 through the opening 51. When mounting the rinsing vessel 10 on the lower plate 8, the rinsing water supply pipe 12 is inserted through the opening 51 into the lower part of the rinsing vessel 10. A liquid-tight seal is created between the outer circumference of the base end part of the rinsing water supply pipe 12 and the edge defining the opening 51 by a sealing ring 52 of an elastic material, such as rubber, elastomer or the like.

The rinsing water supply pipe 12 is a round pipe having a closed tip and an open base end, and provided with the plurality of spouts 12a in a longitudinal arrangement to spout rinsing water in a horizontal direction. The staining basket 13 (FIG. 2) is put in the rinsing vessel 10, and water is spouted through the spout 12a toward the inner surface of a lower part of a side wall of the rinsing vessel 10 to produce water currents in the rinsing vessel 10.

The rinsing water supply pipe 12 is extended in a horizontal direction and detachably fixed by a fixing mechanism shown in FIGS. 14 to 18 and including the coupling nut 18 to the front wall of the water supply duct 16 disposed on a back part of the lower plate 8 and connected to a water supply system. A plurality of pipe fittings 54 (five pipe fittings 54 in the embodiment) are attached to the front wall of the water supply duct 16. Each pipe fitting 54 is provided in a central part of its end wall 55 with an outlet opening 56. A connecting pipe 58 to which a water supply hose connected to the water supply system is connected is attached to a middle part of the lower wall of the water supply duct 16. The base end part of the rinsing water supply pipe 12 is detachably connected to the outlet opening 56. The rinsing water supply pipe 12 is fixedly provided with a flange 59 at a position near its base end. A locating pin 60 is attached to one side of the flange 59 facing the outlet opening 56, and a locating hole 61 for receiving the locating pin 60 is formed in the end wall 55. The locating pin 60 is fitted in the locating hole 61 if the water supply pipe 12 is set in a correct position with the spouts 12a directed in a horizontal direction and the base end part of the water supply pipe 12 is fitted in the outlet opening 56.

When connecting the base end part of the water supply pipe 12 to the outlet opening 56, a gasket 63 (FIG. 14) made of an elastic material is put on the base end part of the water supply pipe 12, the base end part is fitted in the outlet opening 56 so that the locating pin 60 is fitted in the locating hole 61. Then, the coupling nut 18 is put on the water supply pipe 12 from the tip of the water supply pipe 12, and the coupling nut 18 is screwed on the pipe fitting 54 provided in its outer circumference with a male thread to compress the flange 59 and the gasket 63 between the coupling nut 18 and the end wall 55 of the pipe fitting 54 to create a liquid-tight joint between the water supply pipe 12 and the outlet opening 56.

Caps 68 having a cylindrical part 69 provided with an internal thread are screwed on the pipe fittings 54 provided with the external thread 65 in their outer circumferences and having the outlet openings 56 not connected to the water supply pipes 12 to close the outlet openings 56, and the chemical solution vessels 11 are disposed in front of those pipe fittings 54. A gasket is compressed between the inner surface of the end wall 70 of the cap 68 and the end surface of the pipe fitting 54 to prevent the leakage of water through the closed outlet opening 56.

If the staining method to be carried out by the automatic staining apparatus for staining specimens for microscopic examination is changed or the number of staining methods to be carried out simultaneously is changed, and the number of the rinsing vessels 10 needs to be changed, the number of the rinsing vessels 10 can be changed within the number of the outlet openings 56 arranged on the front wall of the water supply duct 16. Although the water supply duct 16 shown in the drawing is provided with five outlet openings 56, the number of the outlet openings 56 of the water supply duct 16 may be greater than five. When a desired number of the rinsing vessels 10 are to be used, a number of the water supply pipes 12 corresponding to the number of the rinsing vessels 10 are fastened to the pipe fittings 54 with the coupling nuts 18, and the rinsing vessels 10 are disposed so that the water supply pipes 12 are inserted in the bottom part of the rinsing vessels 10. The caps 68 are screwed on the pipe fittings 54 having the outlet openings 56 not connected to the water supply pipes 12 to close the outlet openings 56. The chemical solution vessels 11 can be disposed in front of the pipe fittings 54 to which the water supply pipes 12 are not connected.

Demand for specimens for microscopic examination for pathological diagnosis has increased in recent years. The increasing demand for specimens can be met by employing a large staining apparatus, hanging a large staining basket of a capacity greater than that of the conventional staining basket, (called hereafter a small staining basket) on the hooks 25 of the hanger arm 24 (FIG. 1), and using rinsing vessels and chemical solution vessels of a size suitable for receiving the large staining basket therein. Trials were made to immerse two or more small staining baskets held in a longitudinal arrangement or a side-by-side arrangement in the chemical solution or the like contained in the vessel. If the plurality of small staining baskets held in a side-by-side arrangement is immersed in rinsing water, the efficiency of the rinsing operation using water spouted from the water supply pipe 12 is low. Therefore it is preferable to hold the plurality of staining baskets in a longitudinal arrangement. However, the following problem arises if the plurality of staining baskets are held in a longitudinal arrangement.

For example, if a large staining basket of a capacity corresponding to the capacity of two small staining basket is used, it is convenient to stain a large number of specimens at the full staining capacity of the staining apparatus, but such a large staining basket requires troublesome work and reduces staining efficiency when only a small number of specimens need to be stained and the staining apparatus need not operate at its full staining capacity. Therefore it is desirable to enable one small staining basket to be used for staining if the capacity of the small staining basket is large enough to stain a desired number of specimens. Thus, it is preferable to use two or more small basket held in a side-by-side arrangement instead of one large staining basket when busy staining work is required. Naturally, it is effective to use a large staining basket when a very large number of specimens need to be stained.

When specimens contained in two small staining baskets are stained simultaneously, it is convenient to handle the two small staining baskets together instead of handling the two small staining baskets individually. It is preferable to handle two small staining baskets together for a series of operations including moving the empty small staining baskets, inserting glass slides carrying specimens affixed thereto in the small staining baskets, moving the small staining baskets containing the glass slides, and mounting the small staining baskets on the staining apparatus.

Since it is desired to use one large staining basket or one small staining basket or to use a plurality of small staining baskets depending on the degree of busyness of the staining work, the shape and arrangement of the hooks 25 of the hanger arm 24 of the staining apparatus must be changed according to the type and the number of the staining baskets.

If a plurality of small staining baskets are used, it is desirable to handle those small staining basket together.

In an embodiment which will be described below, a suitable adapter meeting a desired staining basket handling condition is selected out of a plurality of kinds of adapters, staining baskets are supported on the selected adapter, and the adapter is hang on the hanger arm of a staining apparatus.

Figure 20:
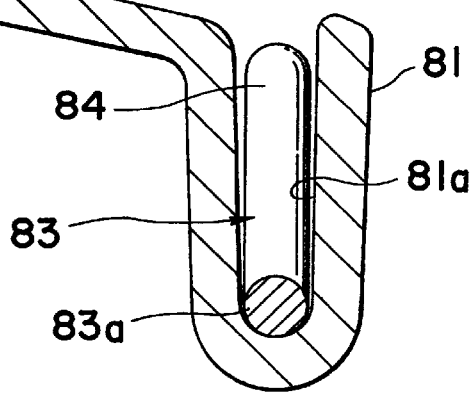
FIG. 20 is an enlarged sectional view taken on line XX—XX in FIG. 19.
Figure 19:
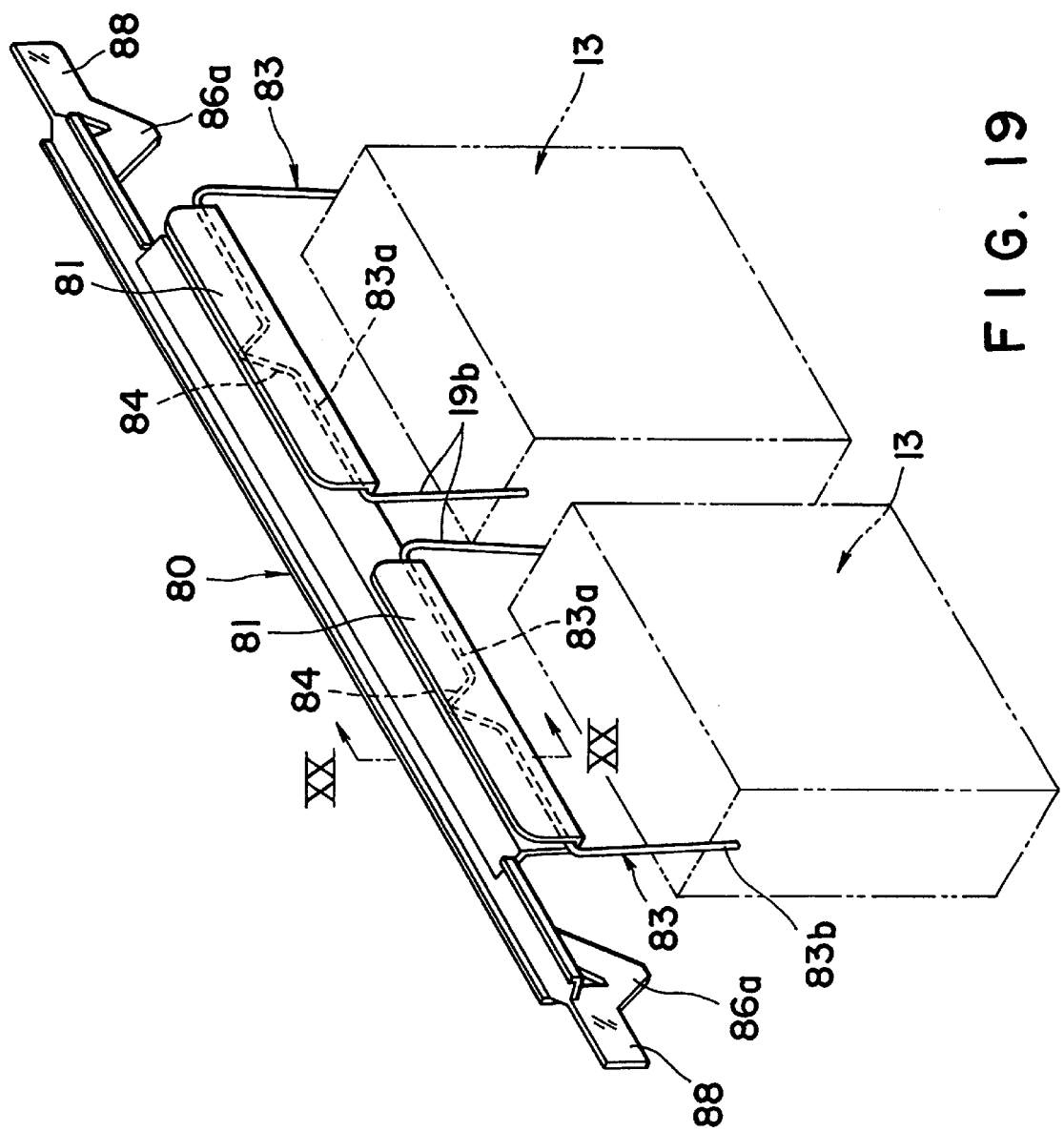
FIG. 19 is a perspective view of an adapter capable of supporting a plurality of staining baskets.

Referring to FIG. 19, an adapter 80 capable of supporting two small staining baskets 13 is hang on the hooks 25, not shown in FIG. 19, of the hanger arm 24 of a staining apparatus. The adapter 80 is provided in its middle part with two hanging parts 81. As shown in FIG. 20, each hanging part 81 forms a narrow groove 81a to receive closely a horizontal section 83a of a handle 83 formed by bending a wire and connected to a staining basket 13. A stopper 84 having the shape of an inverted letter V for preventing the handle 83 from swinging is formed in a part of the horizontal section 83a of the handle 83 of the staining basket 13. The adapter 80 is provided with positioning projections 86a for positioning the adapter 80 on the hooks 25 of the hanger arm 24.

As shown in FIGS. 21 and 22, the opposite end parts 88 of the adapter 80 are engaged with the hooks 25 of the hanger arm 24 so as not to be able to turn. Each hook 25 is provided with a cut 90, and the flat end part 88 of the adapter 80 is fitted closely in the cut 90 of the hook 25.

The adapter 80 thus hooked on the hooks 25 of the hanger arm 24 is restrained from longitudinal movement by the positioning projections 86a and from turning by the engagement of the end parts 88 with the cuts 90, and forms a part of the hanger arm 24.

FIG. 23 shows a flat, horizontal end part of another adapter 80 and a hook 25 provided with a recess suitable for receiving the flat, horizontal end part. The adapter 80 is restrained from longitudinal movement by the engagement of an end edge 80b thereof with the hook 25. Although the end edge 80b is spaced from the hook 25 in FIG. 23, actually, the hooks 25 and the adapter 80 are formed in dimensions so that the opposite end edges 80b are in contact with the hooks 25.

Since the length of the hanging part 81 of the adapter is substantially equal to that of the horizontal section 83a of the handle 83 of the staining basket, the handle 83 is held at a predetermined position on the adapter 80, so that the staining basket can be smoothly and properly transported to the rinsing vessel and the chemical solution vessel and immersed in rinsing water and the chemical solution.

The two staining basket containing the glass slides carrying specimens affixed thereto and to be subjected to the same staining process are supported on the adapter 80 and can be handled together, which improves the efficiency of operations.

The handle 83 is restrained from turning relative to the hanging part 81 by the stopper 84 having the shape of an inverted letter V and restrained from tilting by the side walls of the hanging part 81, and hence the staining baskets 13 are restrained from longitudinal swing motion in the cabinet 7. Since the staining baskets do not swing during transportation, the driving unit 22 (FIG. 1) is able to carry the staining baskets at an increased carrying speed, the staining baskets can be quickly and smoothly moved into the rinsing vessel or the chemical solution vessel, and the staining process can be efficiently carried out.

The foregoing embodiment is capable of operating efficiently by using one large staining basket, one small staining basket or a plurality of small basket according to the degree of busyness of the liquid-processing work. The adapter serves as a reliable means for supporting the staining baskets in the staining apparatus and a convenient means for handling a plurality of staining basket together outside the staining apparatus for operations at an improved efficiency. A plurality of kinds of adapters differing in the size and the number of staining baskets to be held thereon can be selectively used. The adapters are simple in design and can be easily manufactured. Since the staining baskets can be held stationary on the adapter, the staining baskets can be surely moved on the staining apparatus, can be surely immersed in liquids contained in the liquid vessels, and can be moved at high moving speed.

Although the present invention has been described as applied to liquid-processing apparatus for processing specimens for microscopic examination, it is obvious, as mentioned above, that the present invention is applicable to other liquid-processing apparatus for processing vital specimens, such as vital specimen imbedding apparatus, which operate on the same principle as that of the liquid-processing apparatus. It is therefore to be understood that the present invention is applicable to other liquid-processing apparatus for processing vital specimens, such as vital specimen imbedding apparatus.

We claim:

1. A liquid-processing apparatus for processing vital specimens, comprising:

a cabinet;

an elongated horizontal lower plate disposed in said cabinet;

an elongated horizontal upper plate disposed in said cabinet above said lower plate and spaced from said lower plate;

a plurality of liquid vessels mounted on said lower plate and arranged in a line extending in a longitudinal direction along said lower plate;

a plurality of liquid vessels mounted on said upper plate and arranged in a line extending in a longitudinal direction along said upper plate;

a liquid-processing basket for holding the vital specimens;

a driving unit including a hanger arm, said hanger arm being adapted for removably supporting said basket, for moving said basket vertically, and for moving said basket horizontally in a longitudinal direction across said pluralities of liquid vessels along said upper plate and said plate, respectively;

a passage formed in a part of said upper plate and dimensioned so as to permit passage of said hanger arm supporting said basket through said upper plate, said passage connecting spaces extending over and under said upper plate, said spaces being dimensioned so as to permit movement of said basket horizontally in a longitudinal direction across said pluralities of liquid vessels; and control means for controlling said driving unit to move said basket horizontally in a longitudinal direction along said upper plate and said lower plate, and vertically through said passage to immerse said specimens in liquids contained in said liquid vessels by immersing said basket in the liquids contained in said liquid vessels in a predetermined order.

2. The liquid-processing apparatus according to claim 1, wherein the passage is formed in a middle part of the upper plate.

3. A liquid-processing apparatus for processing vital specimens, comprising:

a cabinet;

an elongated horizontal lower plate disposed in said cabinet;

an elongated horizontal upper plate disposed in said cabinet above said lower plate and spaced from said lower plate;

a plurality of liquid vessels mounted on said lower plate and arranged along a line extending in a longitudinal direction along said lower plate;

a plurality of liquid vessels mounted on said upper plate and arranged along a line extending in a longitudinal direction along said upper plate;

a liquid-processing basket for holding vital specimens;

a driving unit including a hanger arm, said hanger arm being adapted for removably supporting said basket, for moving said basket vertically, and for moving said basket horizontally in a longitudinal direction across said pluralities of liquid vessels;

a passage formed in a part of said upper plate and dimensioned so as to permit passage of said basket on said hanger arm so as to connect spaces extending respectively over and under said upper plate, said upper plate being vertically movable relative to said lower plate to change respective heights of said spaces, said spaces being dimensioned so as to permit movement of said basket horizontally in a longitudinal direction across said pluralities of liquid vessels along said lower plate and said upper plate, respectively; and control means for controlling said driving unit so as to move said basket horizontally in a longitudinal direction along said upper plate and said lower plate and vertically through said passage to immerse said specimens in selected liquids contained in said liquid vessels by immersing said basket in said liquids contained in said liquid vessels in a predetermined order.

4. The liquid-processing apparatus according to claim 1, wherein at least one intermediate plate having a second passage formed at a position corresponding to the passage formed in the upper plate is disposed between the upper and the lower plate, and a plurality of liquid vessels are mounted on the intermediate plate.

5. The liquid-processing apparatus according to claim 1, wherein the cabinet has an open front side through which the liquid vessels can be taken out of the cabinet, and the open front side of the cabinet is covered with an openable cover.

6. The liquid-processing apparatus according to claim 5, wherein the openable cover is formed in dimensions such that the openable cover as disposed at a position to cover the open front side of the cabinet leaves an opening through which some of the liquid vessels disposed in the cabinet can be taken out of the cabinet and liquid vessel can be put in the cabinet.

7. The liquid-processing apparatus according to claim 6, wherein the narrow opening is formed so as to enable the liquid vessels placed on the lower plate to be taken out.

8. The liquid-processing apparatus according to claim 6, wherein the control means is provided for setting a plurality of starting positions at which the basket is located at the start of sequential liquid-processing operations, and a plurality of ending positions at which the basket is located at the end of the sequential liquid-processing operations.

9. The liquid-processing apparatus according to claim 1, further comprising:

an openable cover covering an open front side of the cabinet through which the liquid vessels can be taken out of the cabinet;

support members respectively having sliding parts extended in the direction of height of the cover; and hinges each having one end attached to a member of the cabinet defining an upper end of the open front side, and another end attached to the support member;

wherein the cover is supported for sliding along the sliding parts of the support members so that the cover is able to move backward along a top panel of the cabinet when the cover is turned on the hinges through an angle of 90° upward from the open front side of the cabinet.

10. The liquid-processing apparatus according to claim 9, wherein each of the hinges is formed from a plate capable of elastic deformation.

11. The liquid-processing apparatus according to claim 9, further comprising:

arms respectively extending from the sliding parts of the support members toward the cabinet in a state where the openable cover is closed; and dampers each having one end connected to the arm and another end connected to a part of the cabinet near the open front side, for applying pressure of a gas contained therein to the arm.

12. The liquid-processing apparatus according to claim 9, wherein each support member is connected to the openable cover by a spring capable of displacing the openable cover along the sliding part of the support member.

13. The liquid-processing apparatus according to claim 1, wherein the liquid-processing basket is a basket for containing a plurality of glass slides carrying specimens for microscopic examination affixed thereto, and a process to be carried out by the liquid-processing apparatus is a staining process.

14. The liquid-processing apparatus according to claim 13, further comprising:

a rinsing liquid supply duct extended laterally in the space extending over the lower plate;

connecting members having rinsing liquid discharge ports opening toward the front and arranged along the water supply duct;

water supply pipes having base end parts to be detachably connected to the connecting members; and caps to be detachably attached to the connecting members to which any water supply pipes are not connected;

wherein the liquid vessels include rinsing vessels, and each rinsing vessel is provided with a hole through which the water supply pipe is inserted in a liquid-tight fashion into the rinsing vessel when the same rinsing vessel is placed on the lower plate.

15. The liquid-processing apparatus according to claim 14, wherein each of the connecting members is provided with an external thread on an outer circumference thereof, and each of the caps is provided in an inner circumference thereof with an internal thread mating with the external thread of the connecting member.

16. The liquid-processing apparatus according to claim 14 further comprising:

flanges each attached to a base end part of the water supply pipe;

external threads each formed in an outer circumference of the connecting member; and coupling nuts each screwed on the connecting member provided with the external thread on an outer circumference thereof so as to hold the flange in close contact with an end surface of the connecting member.

17. The liquid-processing apparatus according to claim 16, wherein each of the flanges is provided with a locating pin, and each of the connecting members is provided in an end surface thereof with a locating hole for receiving the locating pin therein.

18. The liquid-processing apparatus according to claim 1, further comprising an adapter capable of being unmovably held on the hanger arm and of supporting the liquid-processing basket.

19. The liquid-processing apparatus according to claim 18, wherein the adapter is formed in dimensions suitable for supporting a plurality of liquid-processing baskets in an arrangement.

20. The liquid-processing apparatus according to claim 18, wherein the adapter is provided with holding parts each for receiving a handle attached to the liquid-processing basket from above therein.

21. The liquid-processing apparatus according to claim 1, wherein a process to be carried out by the liquid-processing apparatus is a vital specimen imbedding process.

* * * * *